United States Patent [19]

Barieux et al.

[11] 4,238,612
[45] Dec. 9, 1980

[54] PROCESS FOR THE ISOMERIZATION OF DERIVATIVES OF 3-VINYL-PIPERIDINE

[75] Inventors: Jean-Jacques Barieux, Villeurbanne; Marie-Christine Dubroeucq, Deuil-la Barre; François Rocquet, Viarmes, all of France

[73] Assignee: Pharmindustrie, Gennevilliers, France

[21] Appl. No.: 22,544

[22] Filed: Mar. 21, 1979

[30] Foreign Application Priority Data

Mar. 23, 1978 [FR] France .............................. 78 08449
Feb. 9, 1979 [FR] France .............................. 79 03291

[51] Int. Cl.³ .................. C07D 401/06; C07D 211/32
[52] U.S. Cl. ..................................... 546/153; 546/156; 546/168; 546/176; 546/177; 546/184; 546/192; 546/201; 546/205; 546/206; 546/236; 546/237; 546/238; 546/248
[58] Field of Search ................ 562/401; 546/184, 168, 546/176, 177, 192, 236, 205, 206, 237, 248, 201, 238, 153, 156

[56] References Cited

U.S. PATENT DOCUMENTS 3,753,992  8/1973  Gutzwiller et al. ................... 546/90
3,857,846  12/1974  Gutzwiller et al. ................... 546/90

FOREIGN PATENT DOCUMENTS 2354771  1/1978  France .
4213445  10/1964  Japan ..................................... 562/401

OTHER PUBLICATIONS

Klyne, W. et al., *Atlas of Stereochemistry*, Oxford University Press, N. Y., 1974, p. 14.
Moreau, P. et al., *Bull. Soc. Chim. France*, 1972, No. 2, pp. 649–656.

*Primary Examiner*—Henry R. Jiles
*Assistant Examiner*—Richard A. Schwartz
*Attorney, Agent, or Firm*—Beveridge, Degrandi, Kline & Lunsford

[57] ABSTRACT

A process for the conversion of compounds of the formula:

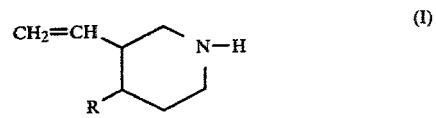

in which R is a hydrogen atom or a substituent and for which the carbon carrying the vinyl group has the rectus configuration, into the corresponding compounds of formula (I) for which the carbon carrying the vinyl group has the sinister configuration, and vice versa, which comprises subjecting a compound of formula (I) for which the carbon carrying the vinyl group has the rectus or sinister configuration, partially or entirely salified, to a heating at a temperature above 50° C. in a protic solvent or a mixture of protic solvents in the presence or absence of formaldehyde, and isolating the compound of formula (I) for which the carbon carrying the vinyl group has the sinister or rectus configuration thus formed.

6 Claims, No Drawings

PROCESS FOR THE ISOMERIZATION OF DERIVATIVES OF 3-VINYL-PIPERIDINE

The present invention relates to a process for the isomerization of derivatives of 3-vinyl-piperidine, and more particularly to a process for the epimerization of the vinyl group in position 3 of these derivatives.

The process of the present invention enables a compound corresponding to the formula:

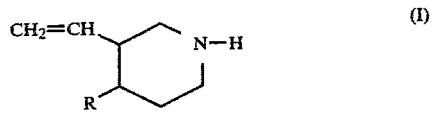

in which R is a hydrogen atom or a substituent and for which the carbon carrying the vinyl group has the rectus configuration (R for short), to be converted into the corresponding compound of formula (I) for which the carbon carrying the vinyl group has the sinister configuration (S for short), and vice versa.

The reaction may be shown diagrammatically as follows:

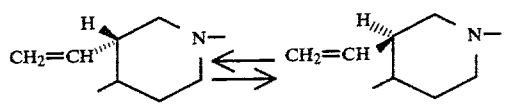

The process according to the invention is especially applicable to the products, derived from the cinchona alkaloids, corresponding to the formula:

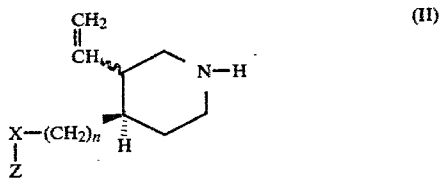

in which n is 1 or 2, X represents a methylene group or a carbonyl group and Z represents an alkoxy group having 1 to 4 carbon atoms, an aromatic residue containing from 6 to 10 carbon atoms, said aromatic residue substituted by chlorine, fluorine, bromine, alkyl 1–4C, alkoxy 1–4C or trifluoromethyl, a heteroaromatic residue containing from 1 to 2 nitrogen atoms and from 3 to 9 carbon atoms or said heteroaromatic residue substituted by chlorine, fluorine, bromine, alkyl 1–4C or alkoxy 1–4C. As an aromatic residue may be particularly mentioned the phenyl group and, as heteroaromatic residues, the 4-quinolyl and 2-indolyl residues, substituted or unsubstituted as described above.

The process according to the invention comprises subjecting a compound corresponding to formula (1), for which the carbon carrying the vinyl group has the rectus or sinister configuration, partially or entirely salified, to a heating at a temperature above 50° C. in a protic solvent or a mixture of protic solvents, in the presence or absence of formaldehyde. By the phrase "partially or entirely salified" is meant the partial or complete formation of a salt with a compound such as hydrochloric acid sulfuric acid, formic acid.

The compound of formula (I), for which the carbon carrying the vinyl group has the sinister or rectus configuration, thus formed is then isolated and purified by conventional methods, physical (chromatography, etc.) or chemical (formation of a salt and regeneration of the free base, etc.).

As examples of protic solvents can be mentioned water and alcohols, particularly the lower alkanols such as methanol and ethanol.

When the process is carried out in the presence of formaldehyde, the amounts of formaldehyde used range preferably from 0.1 mole to 3.0 moles of formaldehyde for each one mole of the compound of formula (I) to be converted. However, it is also possible to carry on the process with amounts of formaldehyde outside this range.

A particularly advantageous method of operation comprises heating the compound of formula (I) at a temperature within the range of from 120° C. to 160° C. in an aqueous medium or in an mixed water+alcohol medium, of which the pH is less than 9 and particularly between 1 and 4, in the absence of formaldehyde. Another advantageous method of operation, particularly useful in the case of compounds which are easily damaged by heat, comprises heating the compound of formula (I) at a temperature within the range of from 50° C. to 80° C., in an aqueous medium or in a mixed water+alcohol medium, the pH of which is less than 9, in the presence of formaldehyde. Such manipulations can be carried out, for example, in an autoclave or a sealed tube. Examples of mixed water+alcohol media which may be used are especially water+ethanol media.

The process according to the invention enables to be prepared in a simple manner, from optically active compounds existing in the natural state or readily accessible from natural products, optically active compounds which do not exist in the natural state and of which the synthesis would be long and difficult.

The compounds obtained by the process of the invention are likely to have therapeutic applications. They can also be used as intermediate products for the synthesis of compounds used therapeutically, especially for the synthesis, according to conventional processes, of the compounds having antiarrythmic and antimalarial activities described in French Pat. No. 2,012,152 and in U.S. Pat. Nos. 3,753,992 and 3,857,846, the disclosures of which are incorporated herein by reference.

The structure of the compounds obtained by the process according to the invention has been determined especially by their nuclear magnetic resonance spectra (NMR for short). This spectrum allows the configuration (S or R) of the carbon carrying the vinyl group (carbon numbered 3) to be identified by the position of the peaks corresponding to the protons numbered 10, 11 and 11' in formula (III) below:

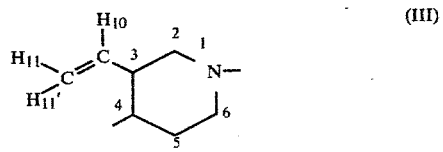

The following examples illustrate the invention without it being limited thereto.

EXAMPLE 1

Preparation of
1-(6-methoxy-4-quinolyl)-3[3(S)-vinyl-4(R)-piperidyl]-1-propanone.

20 ml of distilled water are added to 2.1 g of 1-(6-methoxy-4-quinolyl)-3-[3(R)-vinyl-4(R)-piperidyl]-1-propanone (quinicine) and the pH is brought to 3.5 by addition of an N solution of sulfuric acid. This mixture is introduced into a stainless steel autoclave of 225 ml capacity and is heated for 48 hours at 140° C. The solution is then made alkaline by addition of a 2 N solution of sodium hydroxide and is extracted with ether. The ethereal extract is washed with water, dried over anhydrous sodium sulfate and evaporated to dryness.

The residue obtained (1.7 g) is dissolved in a small amount of a 9/1 toluene-diethylamine mixture, and fixed on a column containing 500 g of silica. It is then eluted with a 9/1 toluene-diethylamine mixture, under a pressure of 4 bars. 0.51 g of the starting substance (quinicine) and 1.08 g of 1-(6-methoxy-4-quinolyl)-3-[3(S)-vinyl-4(R)-piperidyl]-1-propanone are thus isolated. The latter compound is dissolved in methanol and converted into the hydrochloride by addition of an 8 N solution of hydrochloric acid in methanol.

Characteristics of the 1-(6-methoxy-4-quinolyl)-3-[3(S)-vinyl-4(R)-piperidyl]-1-propanone hydrochloride:

Melting point: 171° C.

Rotatory power (measured in water at 25° C.):
$[\alpha]_D^{25} = -33.3°$

NMR spectrum (solvent: deuterochloroform; reference: tetramethylsilane):
$\delta 10$: 5.6 ppm
$\delta 11, 11'$: 5.1 ppm The starting substance, quinicine, may be prepared as indicated by HESSE [Ann. 178 (1875), 244–266], the disclosure of which is incorporated herein by reference.

EXAMPLE 2

Preparation of
1-(4-quinolyl)-3-[3(S)-vinyl-4(R)-piperidyl]-1-propanone.

11.3 g of the oxalate of 1-(4-quinolyl)-3-[3(R)-vinyl-4(R)-piperidyl]-1-propanone (cinchonicine oxalate) are dissolved in 110 ml of deionized water. The solution thus obtained is brought to pH 3.4 by addition of a 5 N solution of hydrochloric acid. This solution is introduced into a 225 ml stainless steel autoclave and heated for 48 hours at 140° C. Then the solution is made alkaline by addition of a 2 N solution of sodium hydroxide and is extracted with ether. The ethereal extract is washed with water, dried over anhydrous sodium sulfate, and evaporated to dryness.

The residue obtained is dissolved in a small amount of a 9/1 toluene-diethylamine mixture, and fixed on a column containing 500 g of silica. It is then eluted with a 9/1 toluene-diethylamine mixture, under a pressure of 4 bars. 2 g of 1-(4-quinolyl)-3-[3(S)-vinyl-4(R)-piperidyl]-1-propanone are thus isolated in the form of an oil. This oil is dissolved in acetone and the above product is converted into its oxalate by addition of a 15 M solution of oxalic acid in acetone. The oxalate is hygroscopic.

Characteristics of 1-(4-quinolyl)-3-[3(S)-vinyl-4(R)-piperidyl]-1-propanone:

NMR spectrum (solvent: deuterochloroform; reference: tetramethylsilane):
$\delta 10$: 5.4 ppm
$\delta 11, 11'$: 5 ppm The cinchonicine, the starting substance, may be prepared as indicated by HESSE [Ann., 178 (1875), 244–266].

EXAMPLE 3

Preparation of
6-methoxy-4-{3-[3(S)-vinyl-4(R)-piperidyl]propyl}-quinoline 2.1 g of 6-methoxy-4-{3-[3(R)-vinyl-4(R)-piperidyl]propyl}-quinoline are dissolved in 20 ml of distilled water. The pH is adjusted to 2 by addition of a 5 N solution of sulfuric acid. This mixture is introduced into a 225 ml stainless steel autoclave and heated for 48 hours at 140° C. Then the solution is made alkaline by addition of a 2 N solution of sodium hydroxide and extracted with ether. The ethereal extract is washed with water, dried over anhydrous sodium sulfate and evaporated to dryness.

The residue obtained (1.9 g) is dissolved in a little 9/1 toluene-diethylamine mixture and fixed on a column containing 500 g of silica. Then it is eluted with a 9/1 toluene-diethylamine mixture, under a pressure of 4 bars. 0.71 g of the starting substance and 0.68 g of 6-methoxy-4-{3-[3(S)-vinyl-4(R)-piperidyl]propyl}-quinoline are thus isolated in the form of an oil. This oil is dissolved in methanol and the above product is converted into its hydrochloride by addition of a 6 N solution of hydrochloric acid in methanol.

Characteristics of the hydrochloride of 6-methoxy-4-{3-[3(S)-vinyl-4(R)-piperidyl]propyl}-quinoline:

Melting point: 151° C.

Rotatory power (measured in water at 25° C.):
$[\alpha]_D^{25} = -31°$

NMR spectrum (solvent: deuterochloroform; reference: tetramethylsilane):
$\delta 10$: 5.4 ppm
$\delta 11, 11'$: 5 ppm The starting substance, 6-methoxy-4-{3-[3(R)-vinyl-4-(R)-piperidyl]propyl}-quinoline may be prepared as follows:

18 g of sodium hydroxide tablets are added to a suspension of 48 g of quinicine in 200 ml of diethyleneglycol and 23 g of an 85% aqueous solution of hydrazine hydrate. The mixture is slowly heated and when the temperature reaches 110° C. the medium is homogeneous. It is then heated for 1 hour at 130° C., then for 2 hours at 150° C. until evolution of nitrogen ceases.

The reaction medium is thrown into 1 liter of iced water. An oil separates which is extracted with 500 ml of ether. The organic phase is decanted, washed, dried over magnesium sulfate, then evaporated. An oil is thus obtained which consists of 6-methoxy-4-{3-[3(R)-vinyl-4(R)-piperidyl]propyl}-quinoline.

EXAMPLE 4

Preparation of the ethyl ester of
[3(S)-vinyl-4(S)-piperidyl]-acetic acid 11.98 g of [3(R)-vinyl-4(S)-piperidyl]-acetic acid ethyl ester (ethyl ester of meroquinene) are dissolved in 60 ml of a 50/50 water-ethanol mixture. The solution is brought to pH 3.5 by addition of an N solution of hydrochloric acid. The mixture is introduced into a 225 ml stainless steel autoclave and heated for 32 hours at 140° C. The water-alcohol solution is evaporated to dryness. The residue obtained (10.1 g) is dissolved in a small amount of a 9/1 toluene-diethylamine mixture, and fixed on a column containing 1000 g of silica. It is then eluted with a 9/1 toluene-diethylamine mixture under a pressure of 3 bars. 2.9 g of the starting product and 4.5 g of the ethyl ester of [3(S)-vinyl-4(S)-piperidyl]-acetic acid in the form of an oil are thus isolated.

Characteristics of the ethyl ester of [3(S)-vinyl-4(S)-piperidyl]-acetic acid:
Rotatory power (measured in chloroform at 25° C.):
$[\alpha]_D^{25} = -35.5°$
NMR spectrum (solvent: deuterochloroform; reference: tetramethylsilane):
$\delta 10$: 5.4 ppm
$\delta 11, 11'$: 5 ppm The ester of meroquinene, the starting substance, can be prepared as indicated by R. LUKES [Chem. Listy, 47, 858 (1953)], the disclosure of which is incorporated herein by reference.

EXAMPLE 5

Preparation of
1-(6-methoxy-4-quinolyl)-3-[3(R)-vinyl-4(R)-piperidyl]-1-propanone (quinicine)

The starting substance consists of 3 g of 1-(6-methoxy-4-quinolyl)-3-[3(S)-vinyl-4(R)-piperidyl]-1-propanone hydrochloride, prepared as indicated in Example 1. The free base is regenerated from this hydrochloride, and 20 ml of distilled water are added to the free base and the pH is brought to 2 by addition of an N solution of sulfuric acid. The mixture is introduced into a 225 ml stainless steel autoclave and is heated for 40 hours at 140° C. Then the solution is made alkaline by addition of a 2 N solution of sodium hydroxide and extracted with ether. The ethereal extract is washed with water, dried over anhydrous sodium sulfate and evaporated to dryness.

The residue obtained (2.22 g), dissolved in a small amount of a 9/1 toluene-diethylamine mixture, is fixed on a column containing 1000 g of silica. Then it is eluted with a 9/1 toluene-diethylamine mixture, under a pressure of 4 bars. 1.03 g of starting substance and 0.25 g of quinicine are thus isolated. The latter is dissolved in methanol and is converted into its hydrochloride by addition of an 8 N solution of hydrochloric acid in methanol.

Characteristics of the quinicine hydrochloride:
Melting point: 183° C.
Rotatory power (measured in water at 25° C.):
$[\alpha]_D^{25} = +44°$
NMR spectrum (solvent: deuterochloroform; reference: tetramethylsilane):
$\delta 10$: 6.48 ppm
$\delta 11$: 5.21 ppm
$\delta 11'$: 5.18 ppm

EXAMPLE 6

Preparation of
6-methoxy-4-{3-[3(S)-vinyl-4(R)-piperidyl]propyl}-quinoline.

0.3 g of 6-methoxy-4-{3-[3(R)-vinyl-4(R)-piperidyl]-propyl}-quinoline dihydrochloride is dissolved in 30 ml of distilled water. The pH is adjusted to 8 by addition of a 1 N solution of sodium hydroxide. The mixture is introduced into a 100 ml stainless steel autoclave and is heated for 24 hours at 160° C. After cooling, the reaction mixture is brought to pH 10 by addition of a 2 N solution of sodium hydroxide, then is extracted with dichloromethane. The organic phase is washed with water, dried over magnesium sulfate and evaporated to dryness.

The residue obtained (0.22 g) contains 75% of 6-methoxy-4-{3-[3(S)-vinyl-4(R)-piperidyl]propyl}-quinoline, which is isolated by high pressure liquid chromatography (eluent: 9/1 toluene-diethylamine mixture) and converted into its hydrochloride by operating as shown in Example 3. Melting point of the hydrochloride: 151° C.

EXAMPLE 7

Preparation of
6-methoxy-4-{3-[3(S)-vinyl-4(R)-piperidyl]propyl}-quinoline 0.3 g of 6-methoxy-4-{3-[3(R)-vinyl-4(R)-piperidyl]-propyl}-quinoline dihydrochloride are dissolved in 31 ml of distilled water. 83 µl of a 37% by weight aqueous solution of formaldehyde are added and the mixture is heated at 70° C. for 20 hours.

After cooling, the reaction mixture is made alkaline by addition of a 2 N solution of sodium hydroxide. An oil separates which is extracted with 50 ml of dichloromethane. The organic phase is washed with water, dried over magnesium sulfate, then evaporated.

0.2 g are obtained of a mixture containing 88% of 6-methoxy-4-{3-[3(S)-vinyl-4(R)-piperidyl]propyl}-quinoline. This compound is isolated and converted into its hydrochloride by operating as shown in Example 6. Melting point of the hydrochloride: 151° C.

EXAMPLE 8

Preparation of
1-(6-methoxy-4-quinolyl)-3-[3(S)-vinyl-4(R)-piperidyl]-1-propanone (epiquinicine)

926 mg of 1-(6-methoxy-4-quinolyl)-3-[3(R)-vinyl-4(R)-piperidyl]-1-propanone hydrochloride (quinicine hydrochloride) are dissolved in 100 ml of distilled water. The pH of the solution is brought to 8.9 by addition of a N/10 solution of sodium hydroxide.

30 ml of this solution are introduced into a 225 ml stainless steel autoclave and are heated for 24 hours at 140° C. Then the solution is made alkaline by addition of a 2 N solution of sodium hydroxide and is extracted with ethyl acetate. The organic phase is washed with water, dried over anhydrous sodium sulfate and evaporated to dryness.

The residue obtained (675 mg) is dissolved in a 9/1 toluene-diethylamine mixture and fixed on a column containing 500 g of silica. Then it is eluted with a 9/1 toluene-diethylamine mixture, under a pressure of 4 bars. 183 mg of 1-(6-methoxy-4-quinolyl)-3-[3(S)-vinyl-4(R)-piperidyl]-1-propanone are thus isolated.

The latter compound is dissolved in methanol and is converted into its hydrochloride by addition of a 8 N solution of hydrochloric acid in methanol.

Characteristics of 1-(6-methoxy-4-quinolyl)-3-[3(S)-vinyl-4(R)-piperidyl]-1-propanone hydrochloride:
Melting point: 171° C.
Rotatory power (measured in water at 25° C.):
$[\alpha]_D^{25} = -33.3°$
NMR spectrum (solvent: deuterochloroform; reference: tetramethylsilane):
$\delta 10$: 5.6 ppm
$\delta 11, 11'$: 5.1 ppm

EXAMPLE 9

Preparation of 1-(6-methoxy-4-quinolyl)-3-[3(S)-vinyl-4(R)-piperidyl]-1-propanone (epiquinicine)

926 mg of 1-(6-methoxy-4-quinolyl)-3-[3(R)-vinyl-4(R)-piperidyl]-1-propanone hydrochloride are dissolved in 100 ml of a 50/50 water-ethanol mixture. 0.29 ml of a 37% aqueous solution of formaldehyde are added. 30 ml of the solution obtained are taken, brought up to pH 4 by addition of a N/10 solution of hydrochloric acid and introduced into a 225 ml stainless steel autoclave. The solution is heated for 24 hours at 70° C., then is made alkaline by addition of a 2 N solution of sodium hydroxide and is extracted with ether. The ethereal extract is washed with water, dried over anhydrous sodium sulfate and evaporated to dryness.

The residue obtained is dissolved in a 9/1 toluene-diethylamine mixture and fixed on a column containing 500 g of silica. Then it is eluted with a 9/1 toluene-diethylamine mixture, under a pressure of 4 bars. 540 mg of 1-(6-methoxy-4-quinolyl)-3-[3(S)-vinyl-4(R)-piperidyl]-1-propanone are thus isolated. This compound is converted into its hydrochloride by operating as shown in Example 8.

The characteristics of the epiquinicine hydrochloride thus obtained are those shown in Example 8.

In formula (I) above in which R is a hydrogen atom or a substituent, said substituent may be a phenyl group, or phenyl group substituted by chlorine, fluorine, bromine, alkyl 1-4C, alkoxy 1-4C, trifluoromethyl, or alkyl 1-4C or a group —(CH$_2$)$_n$—X—Z in which n, X, Z are defined as in formula (II).

What is claimed is:

1. Process for the conversion of compounds of the formula:

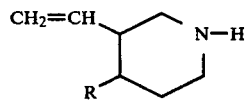

(I)

in which R is hydrogen, phenyl, phenyl substituted by chlorine, fluorine, bromine, alkyl having 1 to 4 carbon atoms, alkoxy having 1 to 4 carbon atoms or trifluoromethyl, alkyl having 1 to 4 carbon atoms or a —(CH$_2$)$_n$—X—Z group wherein n is 1 or 2, X is methylene or carbonyl, and Z is alkoxy having 1 to 4 carbon atoms, phenyl, phenyl substituted by chlorine, fluorine, bromine, alkyl having 1 to 4 carbon atoms, alkoxy having 1 to 4 carbon atoms or trifluoromethyl, or a 4-quinolyl or 2-indolyl residue, unsubstituted or substituted chlorine, fluorine, bromine, alkyl having 1 to 4 carbon atoms or alkoxy having 1 to 4 carbon atoms, and for which the carbon carrying the vinyl group has the rectus configuration, into the corresponding compounds of formula (I) for which the carbon carrying the vinyl group has the sinister configuration, and vice versa, which comprises subjecting a compound of formula (I) for which the carbon carrying the vinyl group has the rectus or sinister configuration, partially or entirely salified, to a heating at a temperature above 50° C. in a protic solvent or a mixture of protic solvents, in the presence or absence of formaldehyde, and isolating the compound of formula (I) for which the carbon carrying the vinyl group has the sinister or rectus configuration thus formed.

2. The process according to claim 1 in which the heating is effected at a temperature in the range of 120° C.-160° C. in an aqueous medium or a mixed water+alcohol medium, of which the pH is less than 9, in the absence of formaldehyde.

3. The process according to claim 2, in which the pH of the medium is between 1 and 4.

4. The process according to claim 1 in which the heating is effected at a temperature within the range of 50° C.-80° C. in an aqueous medium or in a mixed water+alcohol medium, the pH of which is less than 9, in the presence of formaldehyde.

5. The process according to claim 1, 2, 3 or 4 in which the starting substance used corresponds to the formula:

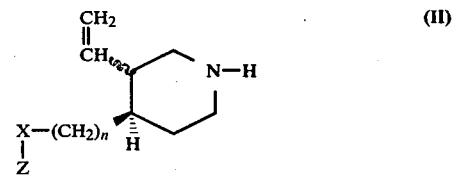

(II)

in which n is 1 or 2, X represents methylene or carbonyl and Z represents alkoxy having 1 to 4 carbon atoms, phenyl, phenyl substituted by chlorine, fluorine, bromine, alkyl having 1 to 4 carbon atoms, alkoxy having 1 to 4 carbon atoms or trifluoromethyl, or a 4-quinolyl or 2-indolyl residue, unsubstituted or substituted by chlorine, fluorine, bromine, alkyl having 1 to 4 carbon atoms or alkoxy having 1 to 4 carbon atoms.

6. The process according to claim 5 in which, in the compound of formula (II), Z is a 4-quinolyl or 2-indolyl residue, unsubstituted or substituted by chlorine, fluorine, bromine, alkyl having 1 to 4 carbon atoms or alkoxy having 1 to 4 carbon atoms.

* * * * *